United States Patent [19]
Wunderlich et al.

[11] Patent Number: 5,957,389
[45] Date of Patent: *Sep. 28, 1999

[54] NEBULISER

[75] Inventors: Erik Wunderlich, Gilching; Robert Waldner, Peiting; Martin Knoch, Berg, all of Germany

[73] Assignee: Paul Ritzau Pari-Werk GmbH, Starnberg, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/785,888

[22] Filed: Jan. 21, 1997

[51] Int. Cl.$^6$ .................................................. A61M 11/00
[52] U.S. Cl. ................................................ 239/338
[58] Field of Search .................... 239/120–122, 239/338, 370; 128/200.11, 200.21, 200.15

[56] References Cited

U.S. PATENT DOCUMENTS

| | | | |
|---|---|---|---|
| 1,951,587 | 3/1934 | Tyler | 239/122 |
| 4,333,450 | 6/1982 | Lester | 128/200.18 |
| 5,549,102 | 8/1996 | Lintl et al. | 239/370 |

FOREIGN PATENT DOCUMENTS

| | | |
|---|---|---|
| 0 540 775 | 5/1993 | European Pat. Off. . |
| 849 172 | 1/1952 | Germany . |
| 1 027 189 | 4/1958 | Germany . |
| 93/01891 | 2/1993 | WIPO ............ 239/338 |

*Primary Examiner*—Kevin Weldon
*Attorney, Agent, or Firm*—Merchant, Gould, Smith, Edell, Welter & Schmidt

[57] ABSTRACT

The invention relates to a nebuliser comprising a nozzle 3 arranged in a nebulising space and an air inlet flue 5 projecting into the nebulising space. The nebulising space is subdivided by a nebulising space divider into two parts, so that proceeding from the nozzle an aerosol flow occurs from the one part into the other. According to the invention, additional impact faces 7 and 8 are provided in the direct vicinity of the nozzle, which have the effect that only the smallest liquid droplets reach into the upper region of the nebulising space and are available to the patient for therapy.

9 Claims, 5 Drawing Sheets

NEBULISER

BACKGROUND OF INVENTION

The invention relates to a nebuliser, especially for use in inhalation therapy, comprising the features of the preamble of patent claim 1.

Such a nebuliser is known from the EP-A-0 540 775. The nebulising space divider which is described for the first time in this nebuliser comprises two portions, of which the impact portion hinders that liquid droplets pass directly from the nebuliser nozzle to the withdrawal orifice of the nebulising space. Liquid droplets settle on the impact portion and are fed back into the liquid reservoir. The leading portion of the nebulising space divider effects an extension of the flow path of the fluid mist during withdrawal and thus provides a homogenisation and drying of the fluid mist.

Aerosols of very high quality can be produced with the known nebuliser. However, on account of the nebulising space divider in the known nebuliser regions exist in which the liquid droplets deposit and are not returned to the liquid reservoir. The amount of liquid which can be withdrawn in the form of a fluid mist or aerosol is therefore only incompletely utilized in proportion to the amount needing to be introduced into the nebuliser. In other words, the yield of the aerosol drug which can be withdrawn is small.

BRIEF SUMMARY OF THE INVENTION

Proceeding from this prior art, the invention is based on the object of developing the known nebuliser so that the yield is increased.

This object is solved by a nebuliser having the features of patent claim 1. Advantageous configurations can be taken from the subclaims.

The invention is described in the following in more detail on the basis of embodiments with reference to the drawings, which show:

DETAIL DESCRIPTION OF THE INVENTION

Figure 1:
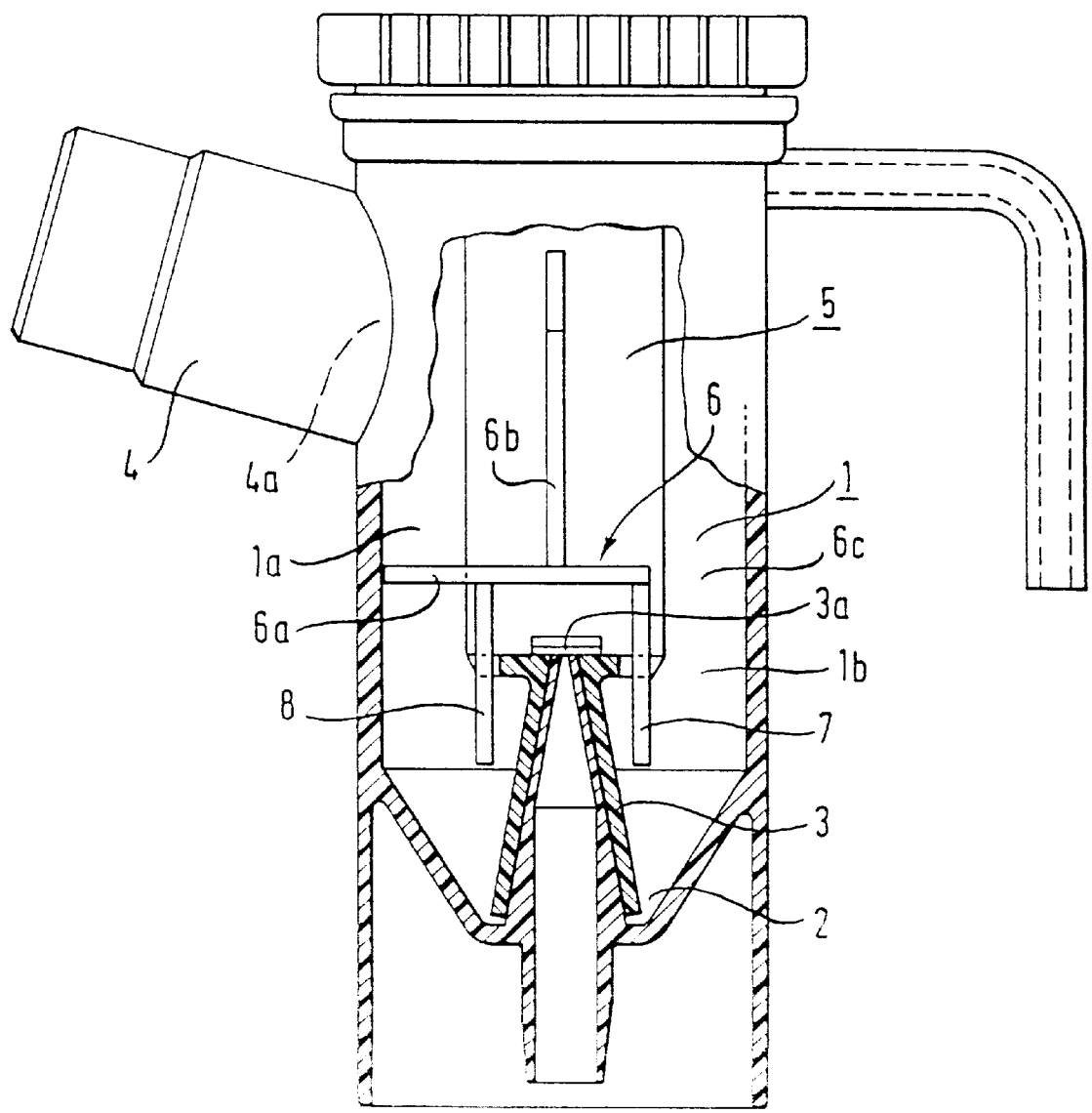
FIG. 1 an embodiment of a nebuliser according to the invention with integrated atomizer nozzle.

The nebuliser shown in FIG. 1 has a cylindrical nebulising space 1, which is closed downwardly by a liquid accumulation region 2 into which the liquid reservoir is filled. With the aid of an atomizer nozzle 3 which is arranged in the center of the cylindrical nebulising space 1, the liquid reservoir is atomized from the liquid accumulation region 2 and in this manner a fluid mist produced in the region of the nozzle orifices 3a which spreads out in the nebulising space 1. The fluid mist is withdrawn from the nebuliser by a patient via an intake member 4. The intake member 4 opens into an orifice 4a of the nebulising space 1. In order to provide the amount of respiratory air necessary for withdrawal of the aerosol, a cylindrical air inlet flue 5 is provided in the center of the nebulising space, through which ambient air is guided into the nebulising space 1. The lower end of the inlet air flue 5 projecting into the nebulising space lies in the vicinity of the nozzle orifices 3a of the atomizer nozzle 3.

The nebuliser shown in FIG. 1 has a nebulising space divider 6 which subdivides the nebulising space 1 into two parts 1a and 1b. The nebulising space divider 6 consists of an impact portion 6a and leading portions 6b, of which only one can be seen in the view of FIG. 1. The impact portion 6a is arranged at the bottom end of the air inlet flue 5 around same, and leaves a through-passage orifice 6c free for the fluid mist on the side of the air inlet flue 5 facing away from the orifice 4a. The leading portions 6b extend in longitidunal direction of the air inlet flue from the outer wall of the air inlet flue 5 to the inner wall of the nebulising space 1. In the same manner the impact portion 6a extends from the air inlet flue 5 to the inner wall of the nebulising space 1.

According to the invention, the nebuliser shown in FIG. 1 comprises at least one essentially flat impact face 7 which is arranged on the side of the impact portion 6a of the nebulising space divider 6 which faces away from the leading portions 6b and which extends essentially perpendicular to the impact portion 6a. The impact face 7 stretches on the two edges extending perpendicular to the impact portion 6a up to the inner wall of the nebulising space 1. As shown in FIG. 1, the impact face 7 lies on the side of the atomizer nozzle facing the orifice 6c of the impact portion 6a.

By means of the impact face 7, it is achieved that excessively large liquid droplets immediately deposit on the surface of the impact face 7 and are returned to the liquid accumulating region 2 before they can pass through the opening 6c of the impact portion 6a into the upper region of the nebulising space 1. In this manner, a settling of the excessively large liquid droplets in the upper region of the nebulising space 1 is avoided from where until now the liquid could no longer return into the liquid accumulating region 2. The yield of withdrawable fluid mist or aerosol is thus increased, since the amount of liquid settling down and not returning to the accumulating region 2 is reduced.

In the nebuliser shown in FIG. 1, a second impact face 8 is arranged on the side of the atomizer nozzle 3 lying opposite the impact face 7. The surface of the impact face 8 lies closer to the nozzle orifices 3a of the atomizer nozzle 3 than the surface of the impact portion 6a. By the arrangement of the second impact face 8, the precipitation and return of large liquid droplets is further supported directly after production by the atomizer nozzle 3.

The impact faces according to the invention effect that only liquid droplets reach into the upper region of the nebuliser I which are so small that they hardly settle on the inner wall of the nebulising space 1 upon flow of fluid mist/air. The aerosol jets spreading out on both sides of the nozzle are guided by the impact faces 7 and 8 to the entire spreading length available, and thus sufficient space for mixing the primary aerosol with the air intaken through the air inlet flue 5 is formed. It is thus ensured that the output aerosol rate is not unnecessarily reduced by deposition of fine droplets.

Figure 2A:
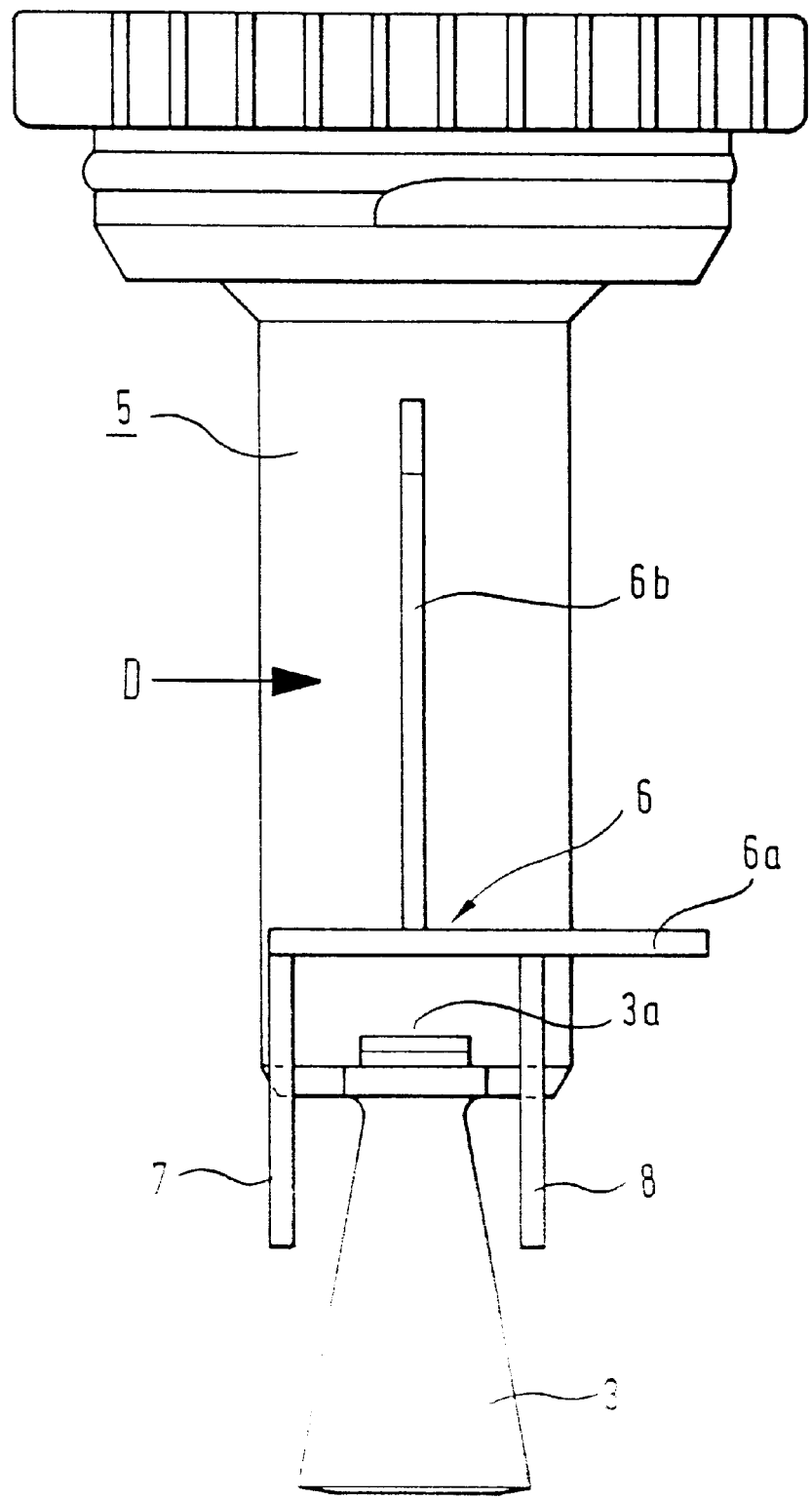
FIGS. 2A to 2C a component of the nebuliser of FIG. 1 in different views.
Figure 2B:
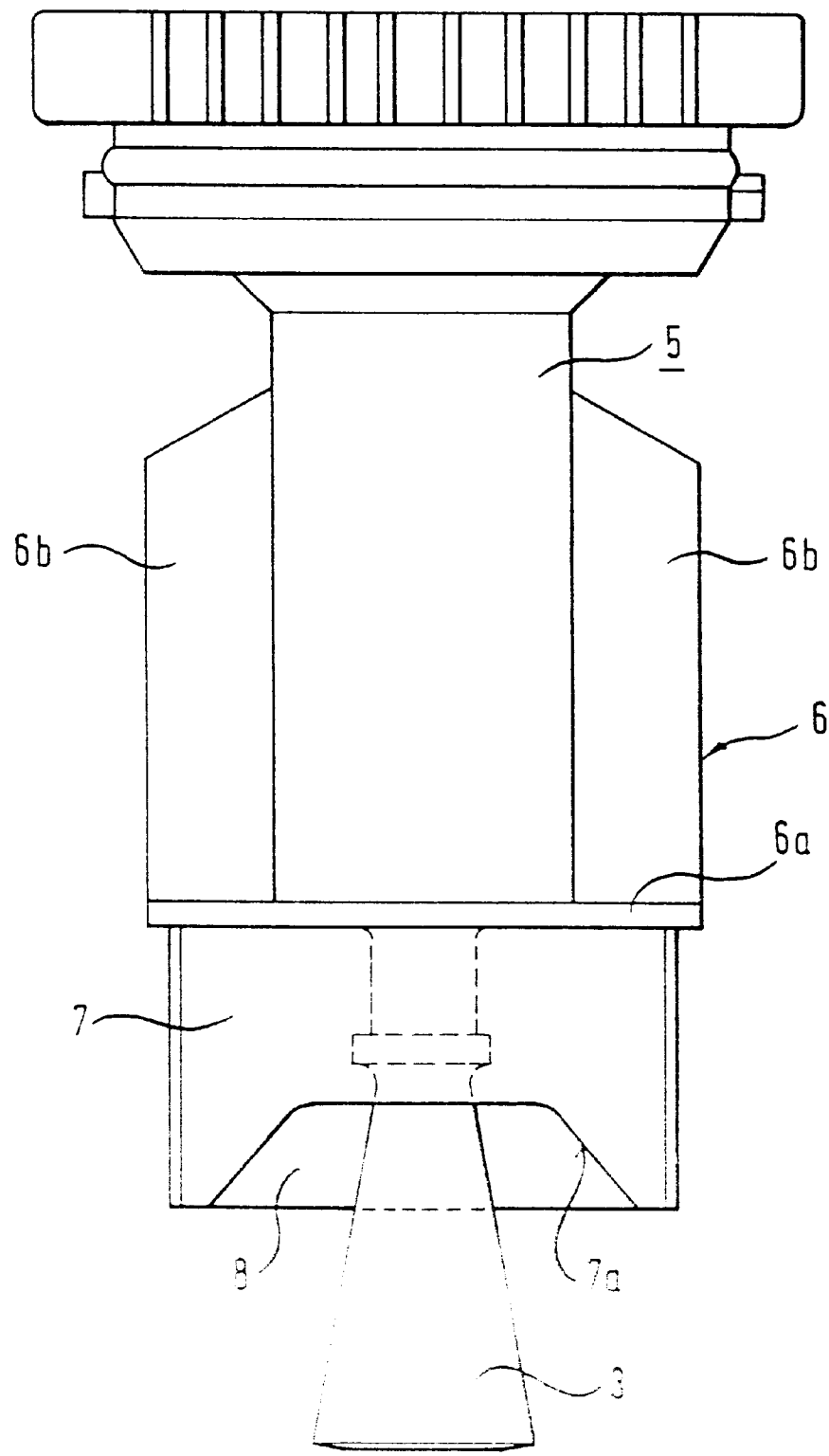
Figure 2C:
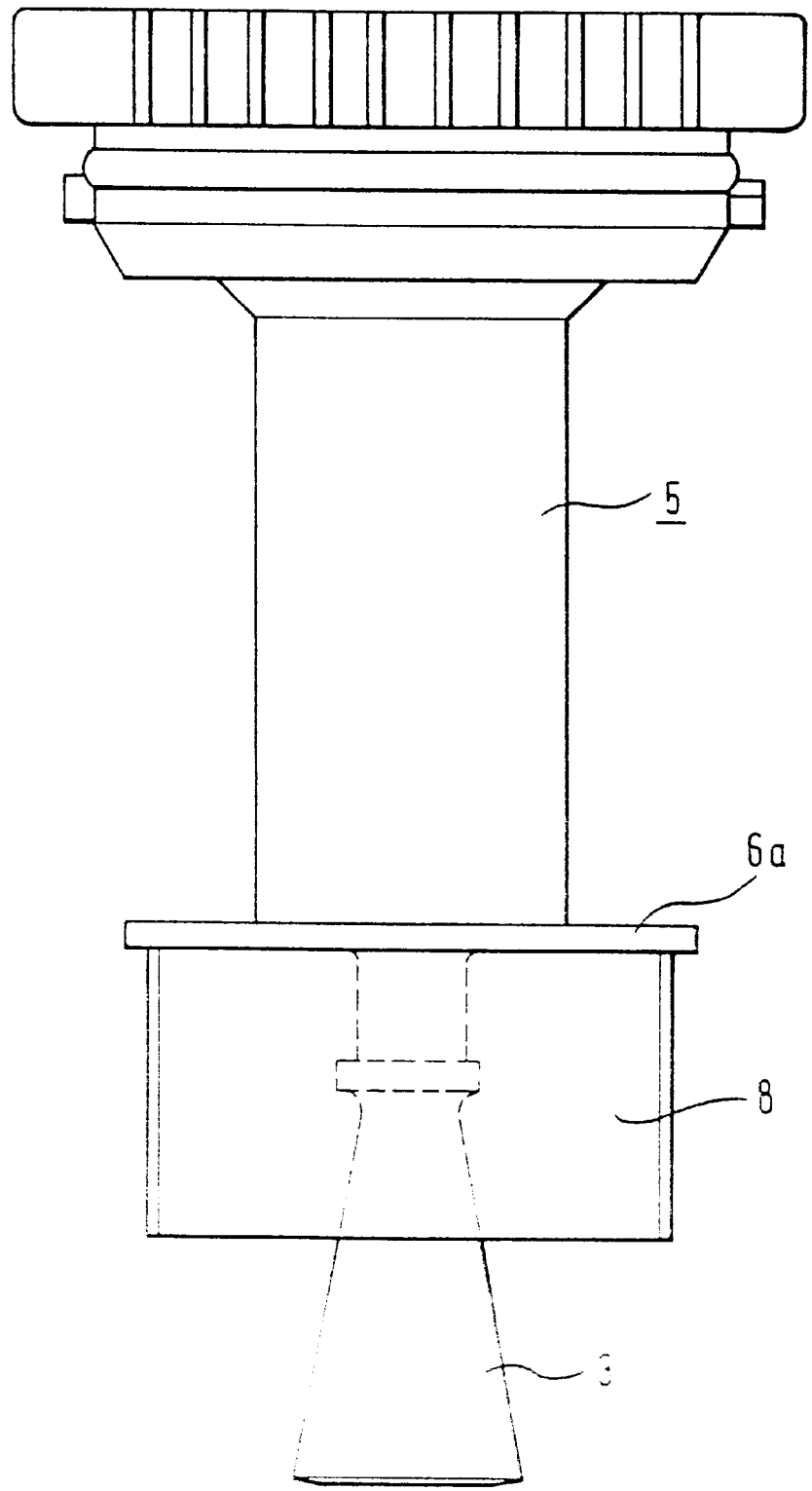
Figure 3A:
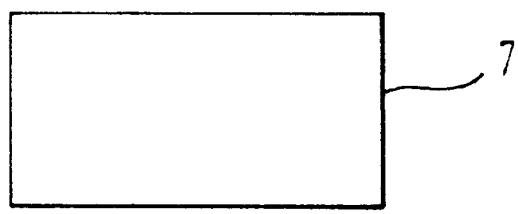
FIGS. 3A to 3E different configurations of the impact faces.
Figure 3B:
Figure 3C:
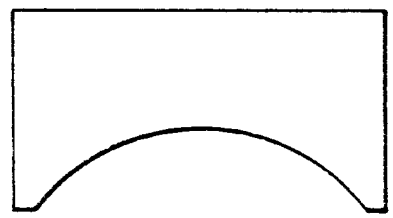
Figure 3D:
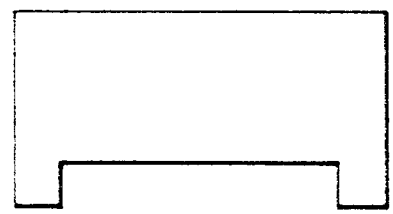
Figure 3E:
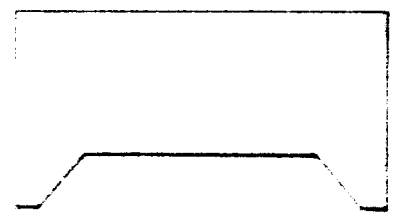

FIG. 2A to 2C reveal the impact faces according to the invention in different views. In this respect, FIG. 2A corresponds with the view of the impact faces in FIG. 1. On both sides of the atomizer nozzle an impact face 7 or 8 respectively is arranged and extends from the impact portion 6a perpendicular to the atomizer nozzle 3. On the opposite side of the impact portion 6a, one of the two leading portions 6b of the nebulising space divider 6 is represented. The leading portion 6b extends in the direction of the longitudinal axis of the air inlet flue 5. In FIG. 2B a view in the direction of the arrow D in FIG. 2A is shown. In this view, both leading portions 6b on the air inlet flue 5 can be seen which extend up to the impact portion 6a and form together therewith the nebulising space divider 6. On the side of the impact portion 6*a* lying opposite the leading portions 6*b* the impact face 7 is visible which extends from the surface of the impact portion 6*a* to the atomizer nozzle 3. It can be further taken from FIG. 2B that in an advantageous configuration, the impact face 7 has a recess 7*a* on the edge facing away from the impact portion 6*a* which exposes in the view of FIG. 2B a view of the impact face 8 behind same in the embodiment. With the recess 7*a*, the possibility exists to adapt the effect of the impact face 7 to the operating parameters of the nebuliser. As compared thereto, the impact face 8 in the embodiment here described is rectangular, as can be taken from the view in FIG. 2C. In any event, the impact faces 7 and 8 verge on the two narrow edges on the inner wall of the nebulising space 1.

FIG. 3A to 3E show different forms of the edge of the impact face 7 facing away from the impact portion 6*a*. In the simplest case, it is a matter of a straight edge as shown in FIG. 3A.

FIG. 3B shows a circularly bent, projecting edge, FIG. 3C a recess in the form of an arc of a circle. FIG. 3D shows a rectangular recess; by inclination of the narrow sides of the recess, a configuration according to FIG. 3E is achieved.

We claim:

1. A nebuliser suitable for use in inhalation therapy, comprising:

a wall defining a nebulising space;

an atomizer nozzle provided in the nebulising space, having an outlet for producing a fluid mist;

an air inlet flue, extending into the nebulising space in a direction substantially parallel to said wall, for delivering outside air to the nebulising space in the area of the outlet of the atomizer nozzle to produce a mixture of fluid mist and air, said wall being provided with an exit orifice spaced longitudinally from the atomizer nozzle for withdrawal of the mixture of fluid mist and air from the nebulising chamber;

a nebulising space divider positioned to divide the nebulising space into a first portion in the area of the exit orifice and a second portion in the area of the atomizer nozzle, whereby the mixture of fluid mist and air flows from the second portion to the first portion for withdrawal through the exit orifice, the nebulising space divider comprising:

an impact portion extending substantially perpendicular to a longitudinal axis of the air inlet flue and disposed around part of the air inlet flue in a shortest path between the outlet of the atomizer nozzle and the exit orifice, and defining a through passage for flow of the mixture of fluid mist and air from the second portion to the first portion;

leading portions extending substantially parallel to the longitudinal axis of the air inlet flue from the impact portion to a position corresponding to the location of the exit orifice, and extending between the wall and the air inlet flue; and a first impact face extending substantially perpendicular to the impact portion in a direction opposite the direction of the leading portions, positioned in the nebuliser at a side of the through passage with respect to the atomizer nozzle.

2. A nebuliser according to claim 1, further comprising a second impact face extending substantially perpendicular to the impact portion in a direction opposite the direction of the leading portions, positioned on an opposite side of the atomizer nozzle with respect to said first impact face.

3. A nebuliser according to claim 1, wherein said first impact face is substantially rectangular in form.

4. A nebuliser according to claim 2, wherein said second impact face is substantially rectangular in form.

5. A nebuliser according to claim 1, wherein said first impact face extends from the air inlet flue to the wall.

6. A nebuliser according to claim 2, wherein said second impact face extends from the air inlet flue to the wall.

7. A nebuliser according to claim 1, wherein an edge of said first impact face distal from the impact portion has a recess in the form of a circular arc or a rectangle.

8. A nebuliser according to claim 1, wherein an edge of said first impact face distal from the impact portion has a recess in a trapezoidal shape that narrows in the direction of the impact portion.

9. A nebuliser according to claim 1, wherein an edge of said first impact face distal from the impact portion has a shape that projects in the form of a circular arc.

* * * * *